US00PP16003P2

(12) United States Plant Patent

Butcher et al.

(10) Patent No.: US PP16,003 P2
(45) Date of Patent: Sep. 27, 2005

(54) *SOLIDAGO* PLANT NAMED 'SOLBUT'

(50) Latin Name: *Solidago cutleri*
Varietal Denomination: Solbut

(75) Inventors: John Butcher, Slough (GB); Paul Gooderham, Diss (GB)

(73) Assignee: Blooms of Bressingham Plant Varieties Ltd., Bressingham (GB)

( * ) Notice: Subject to any disclaimer, the term of this patent is extended or adjusted under 35 U.S.C. 154(b) by 18 days.

(21) Appl. No.: 10/937,827

(22) Filed: Sep. 9, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP8,170 P * 3/1993 Perrine ..... Plt./226
PP12,137 P2 * 10/2001 Danziger ..... Plt./263
2002/0138886 P1 * 9/2002 Danziger ..... Plt./263

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Solidago* plant named 'Solbut', characterized by its compact and upright plant habit; freely basal branching habit; short internodes; dense foliage; dense and bushy appearance; freely flowering habit; daisy-type inflorescences with bright yellow-colored ray florets; and resistance to Powdery Mildew.

1 Drawing Sheet

Botanical designation: *Solidago cutleri.*
Variety denomination: 'Solbut'.

BACKGROUND OF THE INVENTION

The present Invention relates to a new and distinct cultivar of pot-type *Solidago* plant, botanically known as *Solidago cutleri* and hereinafter referred to by the name 'Solbut'.

The new *Solidago* originated from a chance open-pollination in Cippenham, Slough, Berkshire, United Kingdom of an unnamed selection of *Solidago cutleri*, not patented, as the female, or seed, parent with an unknown selection of *Solidago cutleri*, as the male, or pollen, parent. The new *Solidago* was discovered and selected by the Inventor as a single flowering plant in a controlled environment in Cippenham, Slough, Berkshire, United Kingdom in 1994. The selection of this plant was based on its plant habit, ray floret coloration and resistance to Powdery Mildew.

Asexual reproduction of the new *Solidago* by cuttings was first conducted in Bressingham, Diss, Norfolk, United Kingdom in February, 1997. Asexual reproduction by cuttings has shown that the unique features of this new *Solidago* are stable and reproduced true to type in successive generations.

SUMMARY OF THE INVENTION

The cultivar Solbut has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Solbut'. These characteristics in combination distinguish 'Solbut' as a new and distinct pot-type *Solidago:*

1. Compact and upright plant habit.
2. Freely basal branching habit, short internodes and dense foliage; dense and bushy appearance.

3. Freely flowering habit.
4. Daisy-type inflorescences with bright yellow-colored ray florets.
5. Resistance to Powdery Mildew.

Plants of the new *Solidago* are most similar to plants of the female parent selection. In side-by-side comparisons conducted in Bressingham, Diss, Norfolk, United Kingdom, plants of the new *Solidago* differ from plants of the female parent selection in the following characteristics:

1. Plants of the new *Solidago* were larger than plants of the female parent selection.
2. Plants of the new *Solidago* were more uniform and not as straggly as plants of the female parent selection.
3. Ray florets of plants of the new *Solidago* were brighter yellow in color than ray florets of plants of the female parent selection.
4. Plants of the new *Solidago* were resistant to Powdery Mildew whereas plants of the female parent selection were susceptible to Powdery Mildew.

BRIEF DESCRIPTION OF THE PHOTOGRAPH

The accompanying colored photograph illustrates the overall appearance of the new *Solidago* showing the colors as true as it is reasonably possible to obtain in colored reproductions of this type. Colors in the photograph may differ from the color values cited in the detailed botanical description which accurately describe the colors of the new *Solidago.*

The photograph comprises a side perspective view of typical flowering plants of 'Solbut' grown during the summer in an outdoor nursery in Smoketown, Pa.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown and flowered during the summer in Tolar, Tex., in 10-cm containers in an outdoor nursery and under conditions which approximate those generally used in commercial *Solidago* production. Plants were about four months from planting rooted young plants when the botanical description were taken.

Botanical classification: *Solidago cutleri* cultivar Solbut.

Parentage:

*Female, or seed, parent.*—Unnamed selection of *Solidago cutleri*, not patented.

*Male, or pollen, parent.*—Unknown selection on *Solidago cutleri*.

Propagation:

*Type.*—By cuttings.

*Time to initiate roots.*—About 10 days at 20° C.

*Time to produce a rooted young plant.*—About 30 days at 20° C.

*Root description.*—Fine, fibrous; grayed white in color.

*Rooting habit.*—Freely branching; dense.

Plant description:

*Appearance.*—Herbaceous daisy-type perennial pot-type *Solidago*. Compact and upright plant habit; moderately vigorous. Freely basal branching habit, short internodes and densely foliated; dense and bushy appearance.

*Plant height.*—About 21 cm.

*Plant width.*—About 22 cm.

*Lateral branches.*—Quantity per plant: About 12. Length: About 21 cm. Diameter: About 3 mm. Internode length: Short and closely stacked; about 2 mm. Strength: Strong. Texture: Pubescent. Color: 146A.

*Foliage description.*—Arrangement: Alternate to spirally whorled, simple; sessile. Length: About 6.8 cm. Width: About 1.2 cm. Shape: Lanceolate. Apex: Acuminate. Base: Attenuate. Margin: When developing, entire; fully expanded, serrated. Texture, upper and lower surfaces: Sparsely pubescent. Venation pattern: Pinnate. Color: Developing and fully expanded foliage, upper surface: Close to 147A; venation, close to 147A to 147B. Developing and fully expanded foliage, lower surface: Close to 147B; venation, close to 147B to 147C.

Inflorescence description:

*Appearance.*—Daisy-type inflorescence form with lanceolate-shaped ray florets. Inflorescences terminal and axillary. Disk and ray florets develop acropetally on a capitulum. Inflorescences not fragrant. Inflorescences persistent. Inflorescences face upright to outwardly.

*Flowering response.*—Plants flower during the summer in North America.

*Postproduction longevity.*—Inflorescences maintain good color and substance for about 10 to 15 days on the plant.

*Quantity of inflorescences.*—Freely flowering habit with about 140 inflorescences per lateral stem.

*Inflorescence bud.*—Height: About 4 mm. Diameter: About 2 mm. Shape: Elongated ovoid. Color: Close to 144A.

*Inflorescence size.*—Diameter: About 7.5 mm. Depth (height): About 8 mm. Diameter of disc: About 3 mm.

*Ray florets.*—Number of ray florets per inflorescence/arrangement: About seven or eight arranged in a single whorl. Length: About 6 mm. Width: About 2 mm. Shape: Lanceolate. Apex: Obtuse to rounded. Base: Attenuate; fused at base in a short corolla tube. Margin: Entire. Texture, upper and lower surfaces: Smooth, glabrous; satiny. Orientation: Initially upright and incurved; with development, reflexed. Color: When opening and fully opened, upper surface: Close to 9A to 12A. When opening and fully opened, lower surface: Close to 9A.

*Disc florets.*—Arrangement: Massed at center of receptacle. Number of disc florets per inflorescence: About seven. Length: About 5 mm. Diameter, apex: About 1.5 mm. Diameter, base: About 1 mm. Shape: Tubular, salverform, elongated. Apex: Five lobes; lobes acute. Color, immature: Close to 154A. Color, mature: Apex: Close to 9A to 12A. Mid-section: Close to 9A. Base: Close to 144A.

*Phyllaries.*—Quantity per inflorescence: About 15 in two or three whorls. Length: About 3 mm. Width: About 1 mm. Shape: Lanceolate. Apex: Acute. Base: Truncate. Texture, upper and lower surfaces: Smooth, glabrous. Color, upper surface: Close to 144C. Color, lower surface: Close to 144A.

*Peduncles.*—Length, terminal peduncle: About 2.5 mm. Diameter: About 0.75 mm. Aspect: Erect to about 45° from vertical. Strength: Strong; flexible. Texture: Smooth, glabrous. Color: Close to 144A.

*Reproductive organs.*—Androecium: Present on disc florets only. Quantity per disc floret: Five. Anther shape: Elongate. Anther length: About 1 mm. Anther color: Close to 6A. Pollen amount: Moderate. Pollen color: Close to 6A to 9A. Gynoecium: Present on both ray and disc florets. Quantity per floret: One. Pistil length: About 7 mm. Stigma shape: Bilobed; lobes linear. Stigma color: Close to 6A. Style length: About 5 mm. Style color: Close to 5A. Ovary color: Close to 1D.

*Seed.*—Seed production has not been observed.

Disease/pest resistance: Plants of the new *Solidago* have been observed to be resistant to Powdery Mildew. Resistance to pests and other pathogens common to *Solidagos* has not been observed on plants grown under commercial production conditions.

Temperature tolerance: Plants of the new *Solidago* have been observed to tolerate temperatures from about −12 to about 38° C.

It is claimed:

1. A new and distinct cultivar of *Solidago* plant named 'Solbut', as illustrated and described.

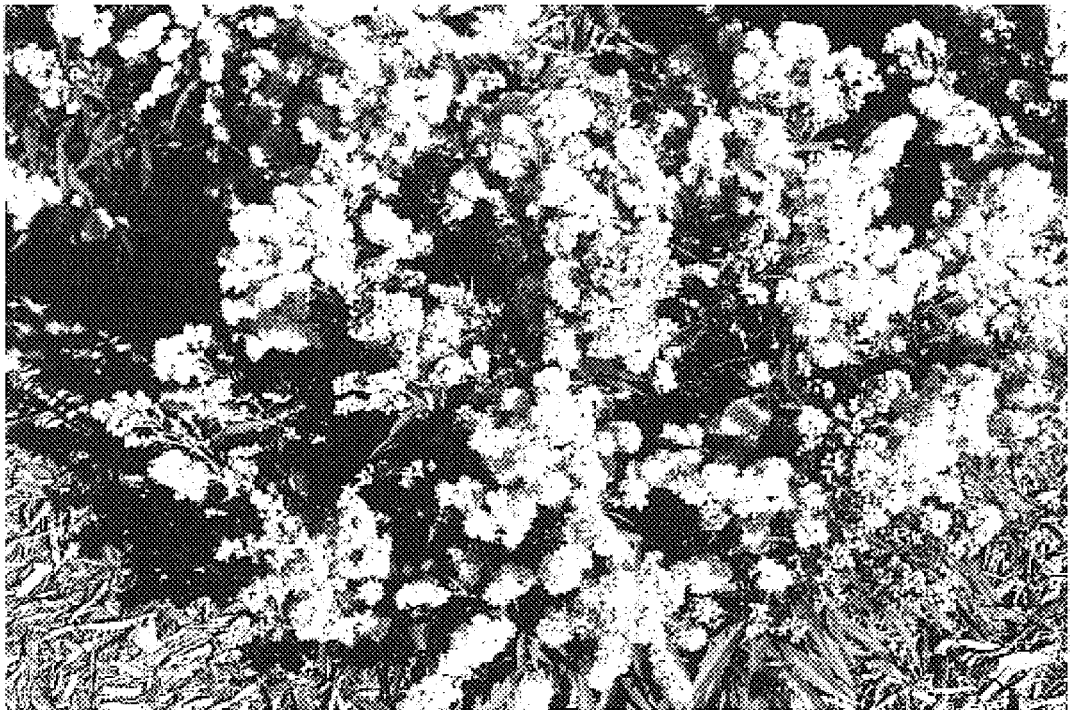

* * * * *